(12) United States Patent
Hinz et al.

(10) Patent No.: US 6,311,565 B1
(45) Date of Patent: Nov. 6, 2001

(54) TECHNIQUES AND EQUIPMENT FOR ASSESSING THE STRUCTURAL INTEGRITY OF SUBTERRANEAN TOWER ANCHOR RODS

(75) Inventors: William R. Hinz; Matthew J. Parker, both of Martinez, GA (US)

(73) Assignee: Westinghouse Savannah River Company, Aiken, SC (US)

( * ) Notice: Subject to any disclaimer, the term of this patent is extended or adjusted under 35 U.S.C. 154(b) by 0 days.

(21) Appl. No.: 09/228,336

(22) Filed: Jan. 11, 1999

(51) Int. Cl.$^7$ .................................................. G01N 29/04

(52) U.S. Cl. ................................................................ 73/801

(58) Field of Search .................... 73/801, 594, 862.53, 73/784, 826, 627, 786, 587, 598, 600, 570 T, 600 T; 405/244; 427/195

(56) References Cited

U.S. PATENT DOCUMENTS

| | | |
|---|---|---|
| 3,600,936 | 8/1971 | Turner . |
| 3,756,071 | 9/1973 | Dory . |
| 3,877,294 | 4/1975 | Shaw . |
| 4,281,547 | 8/1981 | Hinshaw et al. . |
| 4,285,993 * | 8/1981 | Green, Sr. ........................... 427/195 |
| 4,350,044 | 9/1982 | Richardson et al. . |
| 4,380,930 * | 4/1983 | Podhrasky et al. ..................... 73/594 |
| 4,750,117 * | 6/1988 | Gregory ............................... 364/563 |
| 4,858,469 | 8/1989 | Hosgood et al. . |
| 4,904,122 * | 2/1990 | Herbst et al. ........................ 405/260 |
| 5,000,045 * | 3/1991 | Secoy ..................................... 73/801 |
| 5,286,142 * | 2/1994 | Hoyt et al. ............................ 405/244 |
| 5,475,613 | 12/1995 | Itoga et al. . |
| 5,571,966 | 11/1996 | Tsuboi . |
| 5,675,085 | 10/1997 | Hayashi et al. . |
| 5,760,308 | 6/1998 | Beall et al. . |

OTHER PUBLICATIONS

K. Boney, "Getting a Grip on Towers," Cellular Business, Dec. 1995, pp. 42, 46, 48, 52.

F. Langebrake, et al., "Non–destructive Testing of Ground –Anchors of Bridge Structures," International Symposium Non–Destructive Testing in Civil Engineering (NDT–CE), Sep. 26–28, 1995, pp. 453–458.

G. Niles, "In Situ Method of Inspecting Anchor Rods for Section Loss Using the Cylindrically Guided Wave Technique," IEEE Transactions on Power Delivery, vol. 11, No. 3, Jul. 1996, pp. 1601–1605.

* cited by examiner

*Primary Examiner*—Benjamin R. Fuller
*Assistant Examiner*—Oetavia Davis
(74) *Attorney, Agent, or Firm*—Dean W. Russell; Kilpatrick Stockton LLP

(57) ABSTRACT

Techniques and equipment for evaluating structural integrity of buried anchor rods in situ are disclosed. The techniques avoid excavation of soil and avoid, or at least reduce, the possibility of damage to the rods or the concrete in which they may be embedded when evaluations are conducted. Instead, ultrasonic energy is transmitted through the rod from a portable transducer, and returned energy (in either or both of direct and mode-converted states) may be analyzed to assist in detecting flaws, corrosion, wastage, or other degradation of the rod. Data from a field evaluation may be compared with baseline data maintained either for a specific rod or for rods of similar composition and length (or both), and periodic field evaluations of a rod may be used to analyze trends in its structure over time.

12 Claims, 5 Drawing Sheets

TECHNIQUES AND EQUIPMENT FOR ASSESSING THE STRUCTURAL INTEGRITY OF SUBTERRANEAN TOWER ANCHOR RODS

GOVERNMENT RIGHTS STATEMENT

The U.S. government has rights in this invention pursuant to contract number DE-AC09-96SR18500 between the U.S. Department of Energy and Westinghouse Savannah River Company.

FIELD OF THE INVENTION

This invention relates to techniques and equipment for assessing integrity of anchor rods such as those used to support transmission towers and more particularly to methods and associated apparatus for making these assessments without damaging the load-bearing capability of the rods or excavating the terrain in which they may be implanted.

BACKGROUND OF THE INVENTION

The boom in cellular telephone usage and other forms of wireless communication has dramatically increased the number of transmission towers employed today. These towers frequently are guyed, with multiple elongated wire braces spaced about the base of a tower supporting and assisting in counteracting the effects of upper-level winds on the position and integrity of the tower. Several wire braces may terminate in a device such as an equalizer plate, to which a steel rod, typically (although not necessarily) ten to fourteen feet long, is connected at one end. In such situations the other end of the rod may be embedded in concrete and implanted in the ground, thus serving to anchor its associated wire braces and thereby moor the tower.

These anchor rods may, of course, have flaws existing as a consequence of their formation. The acts of connecting an end to an equalizer plate, embedding the opposite end in concrete, and burying a rod partially underground may also create cracks or other flaws in the rod. Because subjected to concrete, soil, and groundwater in use, the anchor rods—even if initially without flaws—further may corrode over time. Wind-related vibrations of the rods additionally cause wallows, or depressions circumscribing their circumferences, in the ground beginning at their entry points therein, so that potentially-harmful surface water may traverse the entire subterranean lengths of the rods.

As the absolute number of guyed structures increases, so too does the number of failures of rods used to anchor the guy wires. According to the December 1995 issue of *Cellular Business* magazine, in the preceding five years approximately nine guyed towers failed because of anchor corrosion. See K. Boney, "Getting a Grip on Towers," *Cellular Business*, December 1995, pp. 42, 46, 48, 52. A study commenced after an injury-causing tower collapse in 1990

> found that 50% to 75% of (anchors) show some signs of corrosion . . . Of that 50% to 75%, maybe 5% to 10% have been corroded to the point that their structural integrity is in question.
>
> Because anchors are built to support specific capacity load, any corrosion also leaves the anchor overstressed. If a 1-inch round steel anchor shaft is corroded to 0.9" or 0.95" instead of its full-inch design, the structural integrity of that anchor is compromised.

Id. at p. 42.

Historically, structural integrity of buried anchor rods was not routinely assessed. As described in Cellular Business, "buried anchors used to be 'out of sight, out of mind.' People didn't see them, so they didn't worry about them." Id. When assessment was necessary, the conventional technique for doing so involved excavating the soil in which a rod was set in order to examine some or all of its length visually. of course, excavating the soil about a rod decreases its load-bearing capability, destabilizing the associated tower until the soil can be replaced. Contacting a galvanized rod with metallic digging equipment, for example, might also damage the rod, and disturbing carcinogenic tars coated on rods might preclude replacement of the soil under existing environmental rules and regulations. Further, of course, mere visual examination of a rod may not result in detection of myriad types of flaws possibly present in it.

SUMMARY OF THE INVENTION

There thus exists significant need for techniques and equipment for evaluating structural integrity of buried anchor rods in situ. The present invention fulfills this need, providing methods useful for in-field (or remote) analysis of rod integrity without excavation of soil. Practicing the methods of the invention additionally is unlikely to damage the rods or the concrete in which they may be embedded. In some circumstances a small amount of metal might need to be removed from the cosmetic weld joining the rod to an equalizer plate (or similar device); this act does not degrade performance of the rod or plate to any measurable extent, however.

Techniques encompassed by the present invention include transmitting ultrasonic (or other suitable) energy from the above-ground end of a rod to its buried end and receiving the energy returned therefrom. Such returned energy, if ultrasonic, manifests in both direct and mode-converted states, either or both may be analyzed to assist in detecting flaws, corrosion, wastage, or other degradation of the rod. Data from a field evaluation may be compared with baseline data maintained either for a specific rod or for rods of similar composition and length (or both), and periodic field evaluations of a rod may be used to analyze trends in its structure over time.

Many conventional metal utility poles or towers are guyed so that the above-ground ("head") ends of any supporting rods are both visible and immediately accessible. Other towers, however, particularly those used in connection with the cellular telephone industry, utilize equalizer plates such as those discussed above. An example of such a plate 10 is shown in FIG. 1. Contrary to the design of many other connectors, the equalizer plate 10 of FIG. 1 contains a recess into which the head end of rod 14 is fitted. The head end thereafter is welded to plate 10, rendering it inaccessible from the exterior of the plate 10.

Because welds typically used for this purpose are not completely of the "full-penetration" type, the plates and head ends typically are not acoustically coupled well. As a consequence, ultrasonic signals transmitted via an equalizer plate to a rod are subject to distortion caused by the poor acoustical coupling. This distortion obviously can affect the results of any analysis performed of a rod, rendering the results ineffective (or at least other than optimal) for decisionmaking about the integrity of the rod.

The invention thus also contemplates preparing the surface of the equalizer plate and head end of a rod, if necessary, to improve the quality of the acoustic signal transmitted through the rod. Such preparation may include removing a portion of the weld or otherwise creating a small flat surface at or adjacent the head end of the rod and perpendicular (or substantially so) to the longitudinal axis of the rod. A portable transducer may then be acoustically coupled to the prepared surface and used to transmit ultrasonic energy through the length of the rod and receive any returned energy for analysis. After the transmissions are complete and the transducer removed, the prepared surface may in some cases be coated with a cold-galvanize compound (such as, but not necessarily, a sprayable material containing zinc) to protect the prepared surface against rust. Thereafter, the prepared surface need merely be dusted to remove dirt or debris thereon before conducting further tests.

Commercially-available anchor rods utilized with some towers are (nominally) either ten or fourteen feet long, similar to those described above. Ten-foot rods have nominal diameter of 1.25 inches, while rods whose nominal length is fourteen feet have nominal diameter of 1.45 inches. Preferred center transmission frequency for evaluation of the former rods is approximately 5 mHz, while that for the latter rods is approximately 2.25 mHz.

Additionally encompassed by the present invention are tools and equipment useful for practicing the innovative analytical methods. One such device, usable when necessary to prepare the surface of the equalizer plate and rod for ultrasonic transmissions, includes a cutting tool for removing a portion of the weld joining the head end of the rod to the plate. The cutting tool is adapted for movement both horizontally and vertically to create, as much as reasonably possible, a flat surface at or adjacent the head end of the rod and perpendicular to the longitudinal axis of the rod. This surface-preparation device may be battery-operated if desired, enhancing its portability for use in the field.

A second device useful in conjunction with the present techniques assists determination of the suitability of the surface preparation. Having shape generally similar to an inverted "L," the device incorporates an interior right angle so that its leg extends perpendicularly from its back. If the prepared surface of the rod is flat and perpendicular to the longitudinal axis, the leg should be flush with the surface when the back rests longitudinally along the circumference of the rod. The leg additionally may be graduated or otherwise marked to assist in determining whether the width of the prepared surface is sufficient to permit good-quality acoustical coupling of a transducer to the rod.

It is therefore an object of the present invention to provide techniques and equipment for evaluating structural integrity of buried anchor rods in situ.

It is another object of the present invention to provide such evaluation methods and apparatus useable without having to excavate soil in which anchor rods are implanted.

It is also an object of the present invention to provide means for enhancing acoustical coupling of a transducer to a rod whose above-ground, or head, end may be welded into a recess and therefore not readily accessible.

It is a further object of the present invention to provide techniques for transmitting ultrasonic energy from at or adjacent the head end of a rod and analyzing any energy returned.

It is additionally an object of the present invention to provide processes for analyzing returned energy in either or both its direct and mode-converted states.

It is yet another object of the present invention to provide evaluation techniques in which present measurements are compared with baseline or prior measurements of either the same rod or a similar class of rods.

It is, moreover, an object of the present invention to provide methods and equipment for exposing a portion of the head end of a rod (or an area adjacent thereto) and thereafter protecting the exposed surface.

Other objects, features, and advantages of the present invention will become apparent with reference to the remainder of the text and the drawings of this application.

BRIEF DESCRIPTION OF THE DRAWINGS

FIGS. 4A–6A are cross-sectional representations of the flaws or effects of corrosion shown, respectively, in FIGS. 4–6.

DETAILED DESCRIPTION

Figure 1:
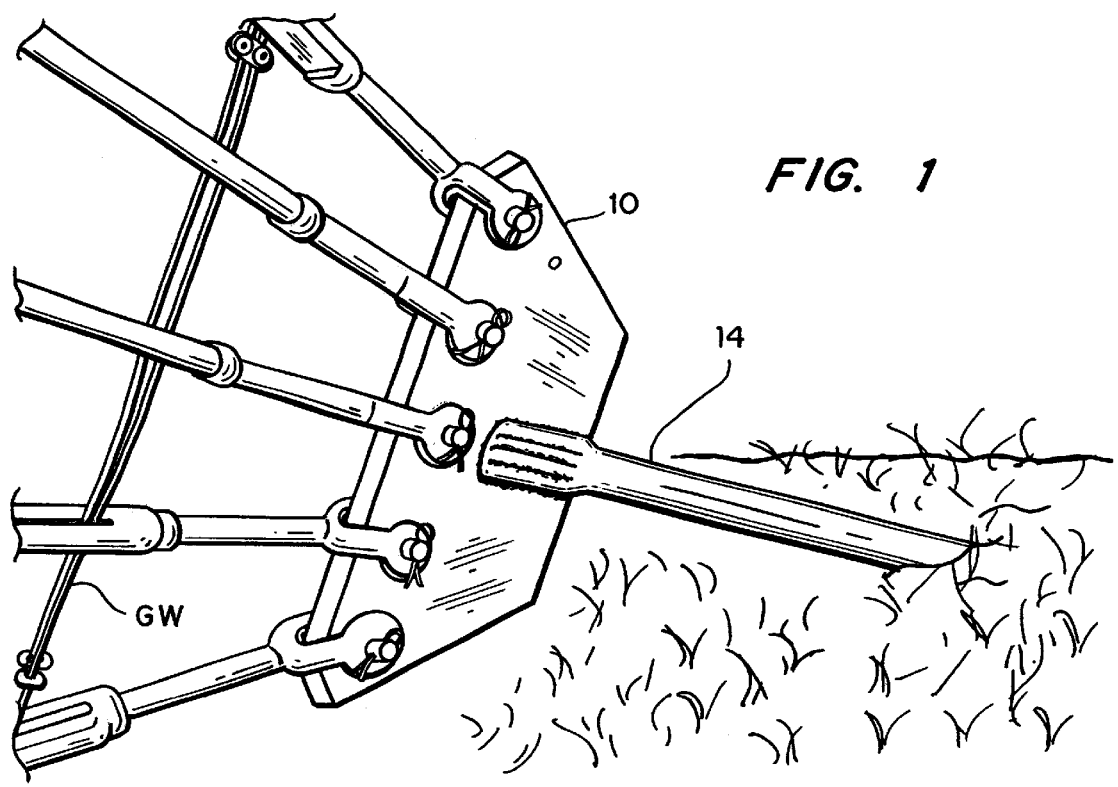
FIG. 1 is a perspective view of an exemplary equalizer plate, guy wires, and anchor rod.

As noted earlier, FIG. 1 illustrates an exemplary equalizer plate 10. Also shown in FIG. 1 are anchor rod 14 and guy wires GW, the latter intended to connect to and support a metal tower or other type of structure. Because each of guy wires GW attaches to a different location of the tower to be supported, it may experience different wind-related and other forces than those to which the other guy wires GW are subjected. Plate 10 is adapted, at least in part, to "equalize" the effects of these different forces and thus is likely to vibrate during times in which it is in use.

Figure 2:
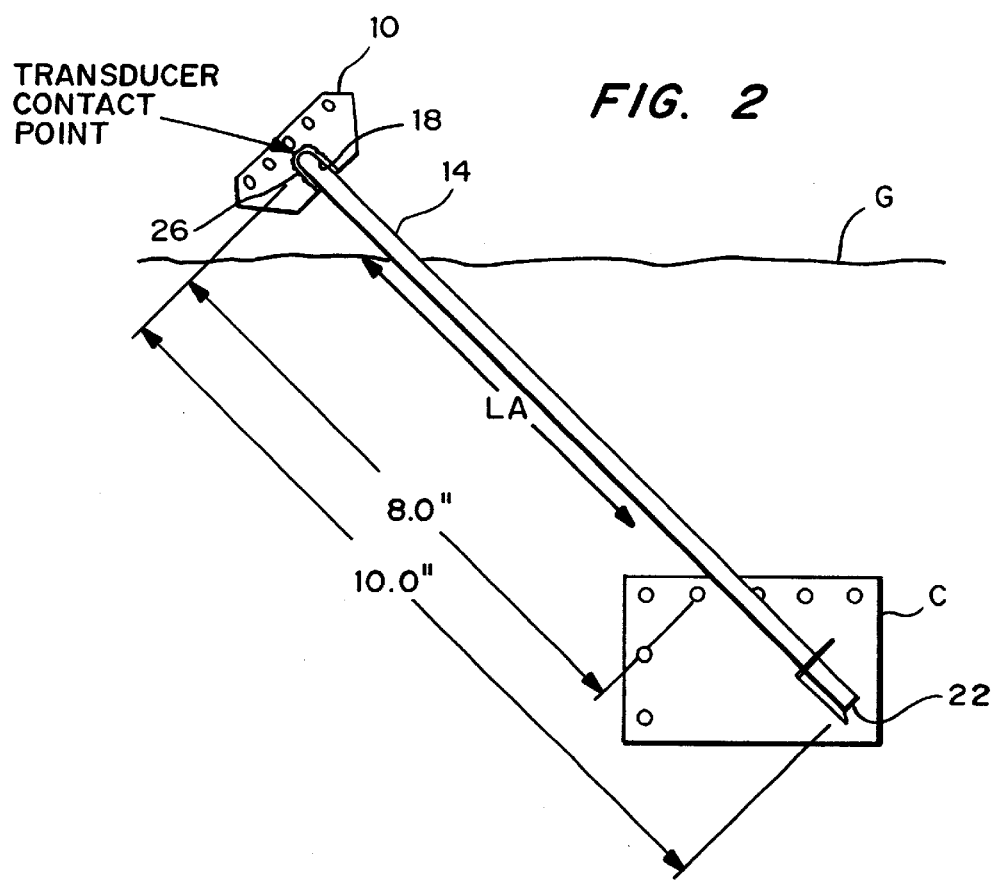
FIG. 2 is a diagrammatic view of an equalizer plate and anchor rod like those of FIG. 1.
Figure 3:
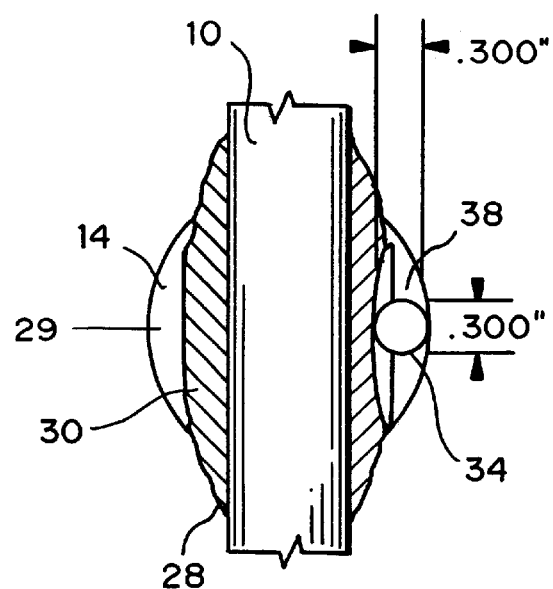
FIG. 3 is a top view of portions of an equalizer plate and anchor rod similar to those of FIGS. 1–2 and showing connection of one to the other.

Attached to plate 10 as shown in FIGS. 1–3 is anchor rod 14. Rod 14 comprises head end 18 and back end 22, the former of which is placed in recess 26 of plate 10. Brazing alloys or other suitable material and any appropriate welding or other technique may be used to connect head end 18 and plate 10. Typically, however, head end 18 is welded to plate 10, with full-penetration welds 28 being employed along the sides of head end 18 and fillet welds 30 (see also FIG. 10) used at the top 29. As a result, rod 14 is relatively rigidly connected to plate 10 with head end 18 inaccessible because of recess 26 and welds 28 and 30. Although techniques and equipment of the present invention are especially useful in circumstances such as these (particularly when head end 18 is not readily accessible), they may be utilized in other situations as appropriate, including in connection with plates or structures other than equalizer plate 10.

Commercially-available rods 14 often are (but need not necessarily be) made of steel approximately ten or fourteen feet long. Certain ten-foot rods 14 have nominal diameter of 1.25 inches, while rods 14 whose nominal length is fourteen feet may have nominal diameter of 1.45 inches. Those skilled in the art will recognize that other rods may be assessed using the innovative techniques and equipment disclosed herein, however.

As illustrated in FIGS. 1–2, much of support rod 14 is usually buried below grade G. Without excavating soil surrounding rod 14, therefore, the majority of it is inaccessible for visual examination. Back end 22, furthermore, may be embedded in reinforced concrete block C underground, rendering it inaccessible for visual review even if excavation occurs.

At least in part because of the lack of full-penetration welds surrounding head end 14, its acoustical coupling to plate 10 typically is inadequate to permit high-quality transmission of ultrasonic energy through both plate 10 and the length of rod 14. However, if head end 18 of rod 14 is or can be made accessible to ultrasonic energy, such energy (or any other suitable form of energy) may be used to assess characteristics of rod 14 in situ. If a transducer probe 34 of small size (e.g. 0.3" diameter) supplies the ultrasonic energy, furthermore, only a relatively small fraction of the area of head end 18 need be accessible to it.

FIG. 3 details a possible placement of transducer probe 34 abutting or adjacent top 29 of head end 18. If top 29 is initially inaccessible, part of weld 30 may be removed to provide access to it. Preferably, the removal process creates a flat surface 38 perpendicular, or nearly so, to the longitudinal axis LA (see FIG. 2) of rod 14. Transducer probe 34 rests flush with surface 38, transmitting ultrasonic energy longitudinally through rod 14. Because the length of rod 14 is substantially greater than its diameter, probe 34 need not necessarily be positioned at the center of top 29 to obtain acceptable results but rather may be placed nearer the circumference of top 29 as, for example, shown in FIG. 3.

In some cases an acoustic couplant such as Panometrix SWC or boiled bees' honey may coat the portion of surface 38 on which transducer probe 34 is positioned. Probe 34 then is activated to transmit ultrasonic energy longitudinally through rod 14. Back end 22 typically acts as a reflector, returning at least some of the transmitted energy to probe 34. Flaws or corrosion present in rod 14 may, however, change or distort the return signals, providing bases for analyzing the integrity of the rod 14. Such analysis may occur in real-time in the field (if, for example, transducer probe 34 is connected to a computational device) or, if desired, signal data may be stored (electronically, on paper, or otherwise) for subsequent processing remote from the site of the rod 14.

After transmissions for a particular rod 14 are complete, surface 38 may be covered or otherwise protected from the ambient environment if necessary or desirable to do so. A preferred method for protecting surface 38 in such circumstances is to cover the surface 38 with a sprayable cold-galvanize coating containing zinc. Experimental results using this type of coating indicate that it need not be removed, but rather merely dusted to remove debris, before the next set of transmissions can be satisfactorily made.

Figure 4:
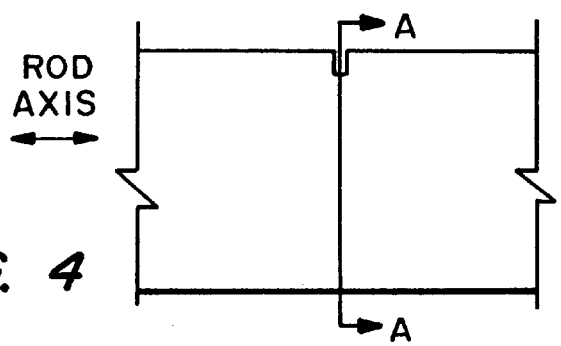
FIGS. 4–6 illustrate types of flaws or effects of corrosion sometimes present in anchor rods such as those of FIGS. 1–3.
Figure 4A:
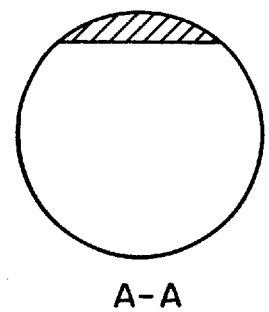
Figure 5:
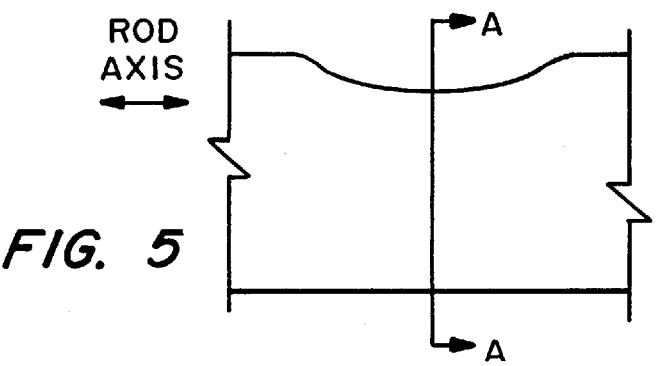
Figure 5A:
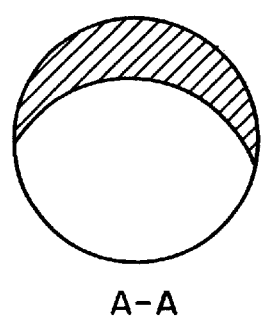
Figure 6:
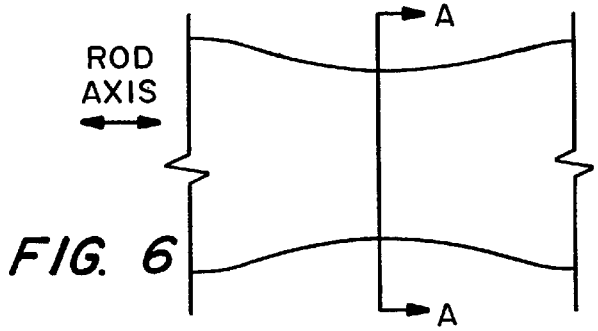
Figure 6A:
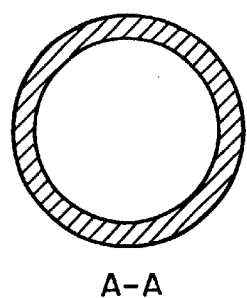

FIGS. 4–6 and 4A–6A diagrammatically illustrate exemplary types of flaws or corrosive effects sometimes encountered with rods 14. FIGS. 4 and 4A, for example, show a planar flaw (i.e. one substantially perpendicular to axis LA), such as when rod 14 is cracked or fractured. FIGS. 5 and 5A, by contrast, illustrate a different type of asymmetrical flaw typical of certain types of corrosion of rod 14. FIGS. 6 and 6A, finally, show a symmetrical flaw associated with rod 14, such as corrosion throughout the circumference of a portion of the length of rod 14.

Determining the existence of these types of flaws or corrosion of a rod 14 preferably (although not necessarily) is accomplished with reference to a baseline or prior set of test results. These earlier test results additionally preferably are obtained for each rod 14 before it is used. If obtaining baseline information for each rod 14 prior to use is inappropriate for any reason, however, it alternatively may be done for one or more samples of the type of rod 14 to be used.

Figure 7:
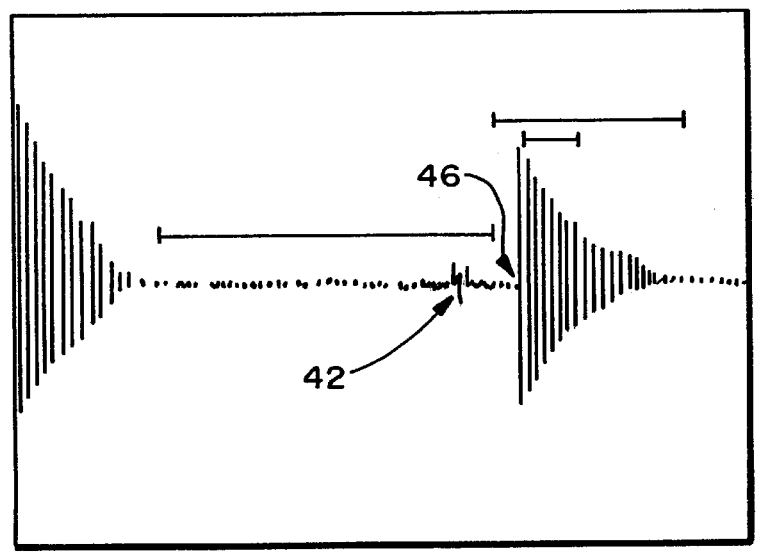
FIG. 7 is a graphical representation of a sample return signal for a anchor rod flawed, for example, similar to FIG. 4.

Additionally, in situ testing of rods 14 is intended to be simply and quickly performed by field personnel. As noted above, ultrasonic energy—from any commercially-available portable supply—may be used to analyze the integrity of rods 14. FIG. 7 illustrates generally a sample return, in which signal strength (amplitude) is plotted on the vertical axis as a function of time. Discontinuity 42 in the graph is consistent with the existence of a planar flaw in rod 14 similar to that shown in FIGS. 4 and 4A, with the flaw located the majority of the distance of rod 14 away from head end 18. In fact, because discontinuity 46 represents the effect of return of ultrasonic energy from back end 22, the position of discontinuity 42 suggests that, in this sample instance, the flaw is located at approximately the point where rod 14 might be embedded below grade in concrete block C.

Figure 9:
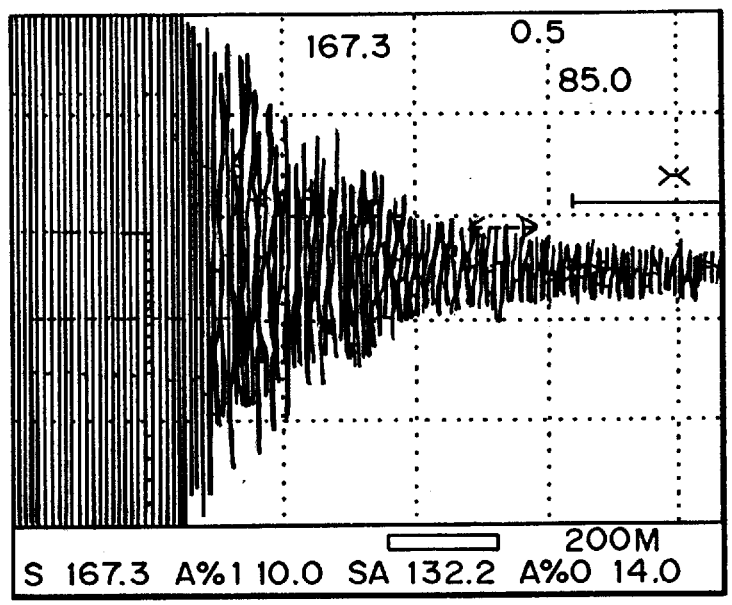
FIG. 9 is a graphical representation of a sample return signal for a anchor rod flawed, for example, similar to FIG. 6.

FIG. 9 generally details a sample plot associated with wastage of the type shown in FIG. 6. Unlike FIG. 7, no sharp discontinuity appears as a result of either a planar flaw or energy having been reflected or otherwise returned off back end 22. Instead, the wastage has caused sufficient diminishment in the amplitude of the transmitted signal such that inadequate energy remains to be received after being returned from back end 22 to permit recognition of the existence of the back end 22. In effect, rod 14 appears incorrectly to be infinitely (or at least indefinitely) long rather than having a defined back end 22.

Figure 8:
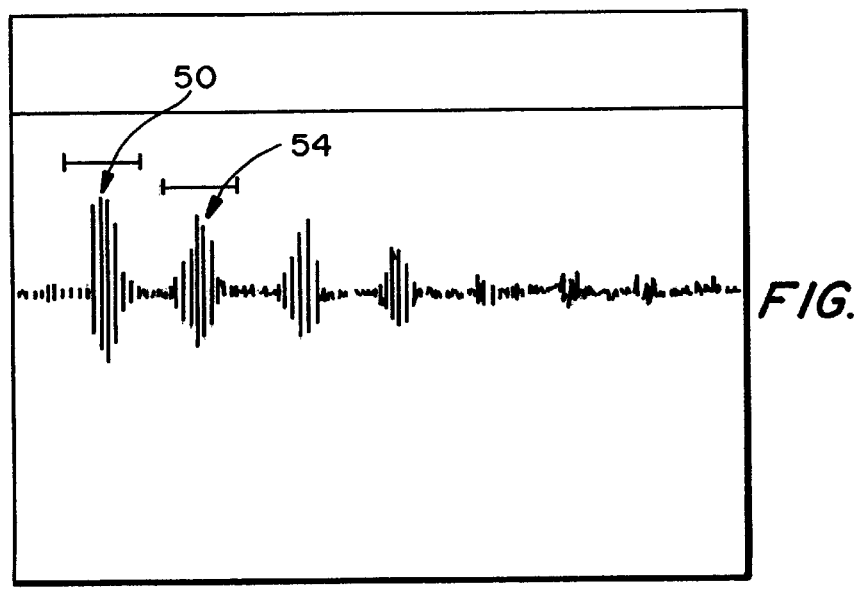
FIG. 8 is an expanded graphical representation of a portion of the return signal of FIG. 7.

FIG. 8 presents an expanded version of portions of the returned signals of FIG. 7, showing generally the quantity and horizontal spacing of mode-converted return signals. Signal set 50, for example, represents the first-arriving longitudinal wavefront, whereas set 54 represents a shear wavefront, etc. Generally regular spacing of the return wavefronts (such as in FIG. 8) suggests the diameter of rod 14 remains regular along its length, while irregular spacing suggests otherwise.

Empirical data indicate that, utilizing the methods described herein, planar flaws may be detected with cross-sectional reductions as low as 5%. Radial wastage, whether symmetric or asymmetric, may be detected with cross-sectional losses as low as 20%. In either event, flaw detection is likely before minimum design loads for rods 14 are encountered. In addition to evaluating the structural integrity of the entire lengths and volumes of rods 14, these techniques may be useful for determining the lengths of the rods 14, determining the minimum diameters of the rods 14 as a function of their lengths, predicting life expectancies for the rods 14, and evaluating new rods 14 prior to installation to ensure only sound rods 14 are installed below grade.

Figure 10:
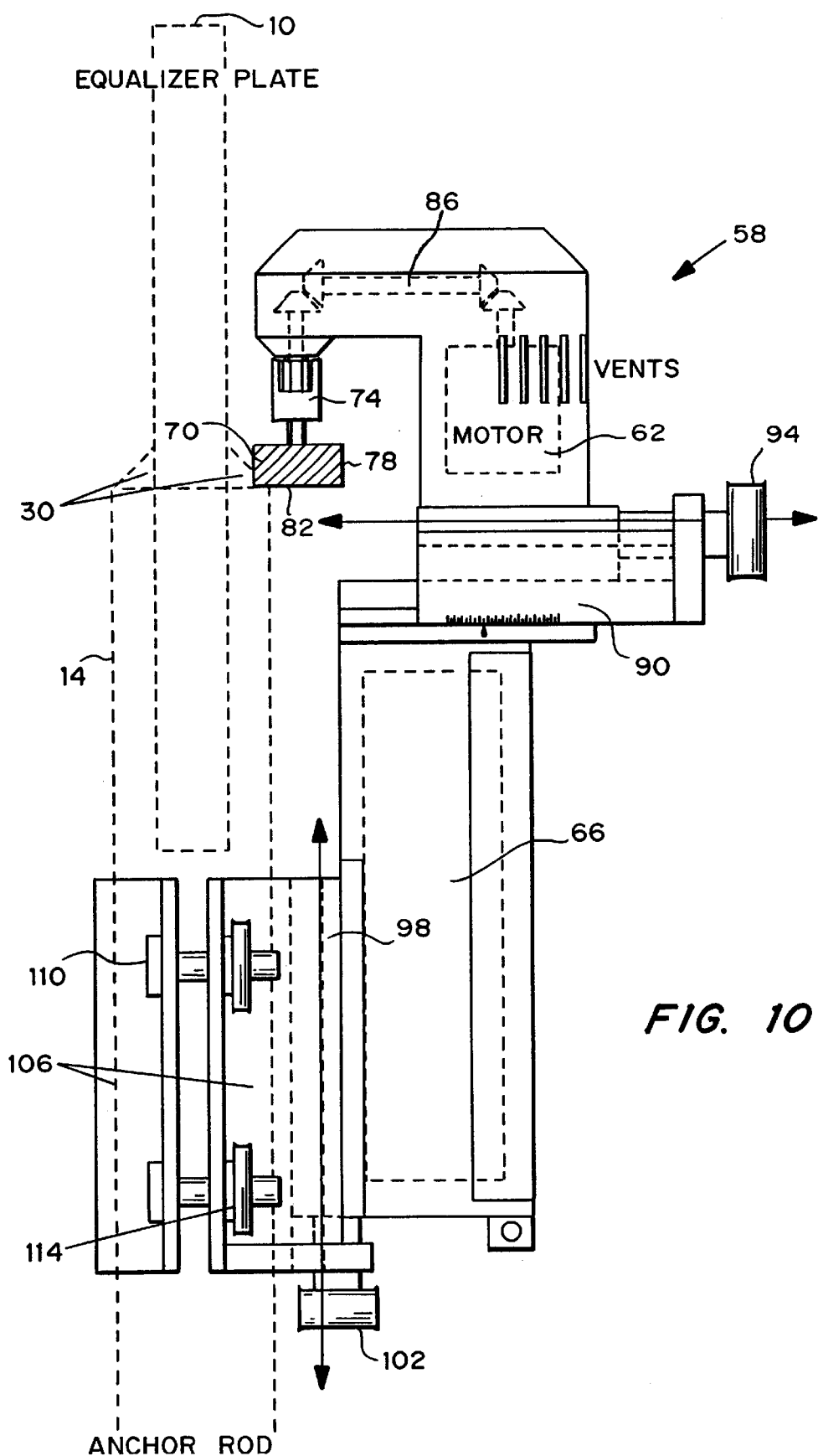
FIG. 10 is a partially-schematicized view of a surface-preparation device useful in connection with the present invention.

Shown in FIG. 10 is a device 58 especially adapted for preparing surface 38 for use in accordance with the present invention. Device 58 may include motor 62 powered by battery 66 (or another suitable power source), with motor 62 operating to turn cutting tool 70 fitted in chuck 74. Tool 70 contains both side and bottom cutting surfaces 78 and 82, respectively, to remove any necessary portions of weld 30 and thereby prepare surface 38. Drive assembly 86, contemplated in one version to be a set of shafts cooperating by means of 45° gears, may connect motor 62 and cutting tool 70 (via chuck 74).

Tool 70 is adapted for movement in two dimensions (for convenience referred to as "horizontally" and "vertically"). Platform 90 and feed knob 94, for example, cooperate to permit adjustment of the horizontal position of tool 70, while an analogous platform 98 and feed knob 102 permit vertical adjustment of tool 70. Device 58 additionally may be clamped to rod 14 for ease of use, with a self-centering fixture 106, fixed studs 110, and anchor nuts 114 being used to effect the clamping.

A second device 118 may also be used to assess the suitability of preparation of surface 38. Shaped like an inverted "L," device 118 comprises leg 122 and back 126, between which a right angle A is defined. When surface 38 is flat and perpendicular to axis LA, interior surface 130 of leg 122 should be flush with surface 38 when interior surface 134 of back 126 rests longitudinally along the circumference of rod 14. Leg 122 additionally may have graduations 138 or otherwise be marked to assist in determining whether the width of the prepared surface 38 is sufficient to permit good-quality acoustical coupling of transducer 34 to rod 14. If desired, device 118 may be detachably connected to device 58 for ease of transport in the field.

Figure 11:
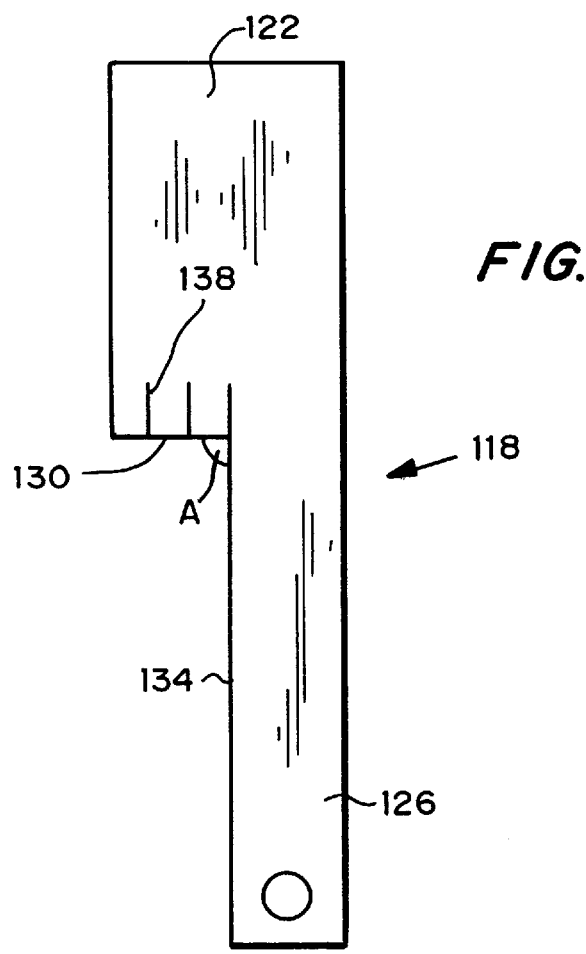
FIG. 11 is a plan view of a second device useful for determining, in part, the quality of the surface preparation.

Those skilled in the art will recognize that apparatus other than devices 58 and 118 may be utilized should preparation of surface 38 be necessary. Likewise, those skilled artisans will recognize that devices 58 and 118 may remain useful for this purpose even if modified and thus need not be configured identically as those shown in FIGS. 10–11. Nonetheless, devices 58 and 118 present apparatus particularly adapted for practicing various of the techniques described herein.

The foregoing is provided for purposes of illustrating, explaining, and describing embodiments of the present invention. Further modifications and adaptation to these embodiments will be apparent to those skilled in the art and may be made without departing from the scope of spirit of the invention. Additionally, by this reference applicants incorporate herein in its entirety the article G. Niles, "In Situ Method of Inspecting Anchor Rods for Section Loss Using the Cylindrically Guided Wave Technique," *IEEE Transactions on Power Delivery*, Vol. 11, No. 3 , July 1996, pp. 1601–1605, which discusses inspection of certain rods whose above-grade ends are exposed.

We claim:

1. A system for assessing, without excavation, structural integrity of an anchor having initially unexposed first and second ends and adapted in use to support a guyed tower with the first end buried below grade, comprising:

a. means for transmitting a signal of an amplitude and type effective to traverse from the second end of the anchor to the first end and provide a return signal at the second end unless prevented from doing so because of one or more flaws in the anchor, and b. means for assessing the structural integrity of the anchor by analyzing the return signal.

2. A system according to claim 1 in which the signal is ultrasonic, the anchor is an elongated metal rod, and the second end is welded in use to a plate so as to be obscured from view.

3. A method of assessing without excavation, structural integrity of an anchor having initially unexposed first and second ends and adapted in use to support a guyed tower with the first end buried below grade, comprising the steps of;

a. transmitting a signal of an amplitude and type effective to traverse from the second end of the anchor to the first end and provide a return signal at the second end unless prevented from doing so because of one or more flaws in the anchor; and b. assessing the structural integrity of the anchor by analyzing the return signal.

4. A method according to claim 3 in which the step of transmitting a signal comprises transmitting an ultrasonic signal from a location at or adjacent the second end of an elongated metal rod forming the anchor, the second end being welded in use to a plate.

5. A method of assessing in situ integrity of an elongated anchor rod having first and second ends, the first end of which is positioned below grade and the second end of which is above ground in use but sufficiently unexposed so as to preclude high-quality acoustical coupling comprising the steps of:

a. exposing at least a portion of the second end;

b positioning a source of ultrasonic energy on the exposed portion of the second end;

c. transmitting ultrasonic energy through the rod toward the first end; and d. receiving any ultrasonic energy returned to the source.

6. A method according to claim 5 further comprising the step of analyzing the returned ultrasonic energy.

7. A method according to claim 5 further comprising the step of coating the exposed second end with a protective material after receiving any ultrasonic energy returned to the source.

8. A method according to claim 5 in which the second end is welded to a plate by a weld and the step of exposing at least a portion of the second end comprises removing a portion of the weld.

9. A method according to claim 6 in which the step of analyzing the returned ultrasonic energy comprises comparing the returned ultrasonic energy with that obtained from a prior or baseline test.

10. A method according to claim 6 in which the step of analyzing the returned ultrasonic energy comprises examining direct and mode-converted components of the energy.

11. A method according to claim 8 further comprising the step of coating the exposed portion of the second end with an acoustic couplant.

12. A method of assessing, without excavation, structural integrity of an elongated metal anchor rod defining a longitudinal axis and having first and second ends, the first end implanted underground and embedded in concrete and the second end welded to an equalizer plate, comprising the steps of:

a. removing a portion of material by which the second end is welded to the equalizer plate so as to create an at least substantially flat surface at or adjacent the second end at least substantially perpendicular to the longitudinal axis;

b. assessing flatness and perpendicularity of the surface;

c. coating an acoustic couplant onto the surface;

d. positioning a portable transducer on the surface;

e. activating the transducer so as to transmit ultrasonic energy through the anchor rod toward the first end;

f. receiving at the transducer ultrasonic energy returned to the second end;

g. analyzing direct and modeconverted components of the returned ultrasonic energy; and h. coating the surface with a cold-galvanize compound.

* * * * *